United States Patent
Chakravarthy et al.

(10) Patent No.: US 9,706,938 B2
(45) Date of Patent: Jul. 18, 2017

(54) SYSTEM AND METHOD TO DETERMINE PREMATURE VENTRICULAR CONTRACTION (PVC) TYPE AND BURDEN

(71) Applicant: Medtronic Monitoring, Inc., San Jose, CA (US)

(72) Inventors: Niranjan Chakravarthy, Eden Prairie, MN (US); Abhi Chavan, Maple Grove, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 0 days.

(21) Appl. No.: 14/926,458

(22) Filed: Oct. 29, 2015

(65) Prior Publication Data
US 2017/0119274 A1    May 4, 2017

(51) Int. Cl.
*A61B 5/00*      (2006.01)
*A61B 5/0468*    (2006.01)
*A61B 5/04*      (2006.01)

(52) U.S. Cl.
CPC ........ *A61B 5/0468* (2013.01); *A61B 5/04012* (2013.01)

(58) Field of Classification Search
CPC .............. A61B 5/0468; A61B 5/04012; A61B 5/0452–5/0472
See application file for complete search history.

(56) References Cited

U.S. PATENT DOCUMENTS

| | | | |
|---|---|---|---|
| 7,181,282 B1 | 2/2007 | Province et al. | |
| 7,715,906 B2 | 5/2010 | Krause et al. | |
| 8,027,722 B1 * | 9/2011 | Nabutovsky | A61B 5/0468 607/14 |
| 8,483,813 B2 | 7/2013 | Zhang et al. | |
| 8,983,586 B2 | 3/2015 | Zhang | |
| 9,107,571 B2 | 8/2015 | Strauss et al. | |
| 2009/0318820 A1 * | 12/2009 | Toledo | A61B 5/04014 600/509 |

(Continued)

OTHER PUBLICATIONS

Baman, et al., "Relationship between burden of premature ventricular complexes and left ventricular function", Heart Rhythm, vol. 7, 2010, pp. 865-869.

(Continued)

*Primary Examiner* — Scott Getzow
(74) *Attorney, Agent, or Firm* — Billion & Armitage; Michael A. Collins (57) ABSTRACT

A system and method of monitoring and reporting premature ventricular contractions (PVCs) detected in a patient is described. The method includes monitoring an electro-cardiogram (ECG) signal of the patient with an adherent device that includes a plurality of electrodes. Premature ventricular contraction (PVC) beats are detected based on the monitored ECG signal, and ECG episodes associated with detected PVC beats are stored for subsequent analysis. A morphology signal is calculated by quantifying the stored ECG episodes associated with detected PVC beats, wherein the morphology signal numerically represents the shape of the detected PVC beat. The PVC beats are then numerically clustered based on the calculated morphology signals to group PVC beats having a similar morphology or shape, and a report is generated based on the clustering of the PVC beats.

15 Claims, 10 Drawing Sheets

(56) References Cited

U.S. PATENT DOCUMENTS

| | | | |
|---|---|---|---|
| 2013/0190635 A1* | 7/2013 | Shen | G06K 9/00503 |
| | | | 600/521 |
| 2013/0331900 A1 | 12/2013 | Levine | |
| 2015/0126822 A1 | 5/2015 | Chakravarthy et al. | |
| 2015/0164359 A1* | 6/2015 | Amirim | A61B 5/0472 |
| | | | 600/515 |

OTHER PUBLICATIONS

Cha, et al., "Premature Ventricular Contraction-Induced Cardiomyopathy a Treatable Condition", Circulation: Arrhythmia and Electrophysiology, vol. 5, 2012, pp. 229-236.

Garcia, et al., "Arrhythmia Recognition, The Art of Interpretation", Jones & Bartlett Learning, First Edition, Nov. 12, 2003, 633 pages.

Hasdemir, et al., "Tachycardia-induced cardiomyopathy in patients with idiopathic ventricular arrhythmias: the incidence, clinical and electrophysiologic characteristics, and the predictors", J Cardiovasc Electrophysiol, vol. 22, 2011, pp. 663-668.

Kanei, et al., "Frequent premature ventricular complexes originating from the right ventricular outflow tract are associated with left ventricular dysfunction", Annals of Noninvasive Electrocardiology, vol. 13, 2008, 81-85.

Niwano, et al., "Prognostic significance of frequent premature ventricular contractions originating from the ventricular outflow tract in patients with normal left ventricular function", Heart, vol. 95, 2009, pp. 1230-1237.

"Premature Ventricular Complex (PVC)", http://lifeinthefastlane. com/ecg-library/basics/pvc/, Downloaded Dec. 2016.

Fischer, et al., "Testing the Quality of 12 Lead Holter Analysis Algorithms", Computers in Cardiology, 35, 2008, 453-456.

Lehmann, et al., "A novel multi-lead method for clustering ventricular ectopic heartbeats", 2011 Computing in Cardiology (CINC 2011): Hangzhou, China, Sep. 18-21, 2011, IEEE, Piscathaway, NJ, Sep. 18, 2011, 749-752.

Daubechie, "Ten Lectures of Wavelets", https://jqichina.files. wordpress.com/2012/02/ten-lectures-of-waveletsefbc88e5b08fe6b3a2e58d81e8aeb2efbc891.pdf, Jun. 1, 1992.

Search Report and Written Opinion from corresponding application for PCT Application No. PCT/US2016059094, mailed on Feb. 9, 2017.

* cited by examiner

SYSTEM AND METHOD TO DETERMINE PREMATURE VENTRICULAR CONTRACTION (PVC) TYPE AND BURDEN

TECHNICAL FIELD

The present disclosure is related in general to patient monitoring and in particular to monitoring, detecting and diagnosing premature ventricular contraction (PVC) type and burden.

BACKGROUND

Premature ventricular contractions (PVCs) are premature depolarizations that originate in the ventricle. PVCs can cause symptoms such as palpitations, chest pain and syncope. However, PVC is a ubiquitous heart rhythm, occurring both in healthy patients as well as those with underlying heart disease. PVC morphology (i.e., shape) depends on the ectopic ventricular pacer location that triggered the contraction and the depolarization route taken by the contraction. PVCs that originate at the same ectopic pacer location and depolarize via the same route are known as unifocal PVCs, while PVCs that originate from multiple ectopic pacer locations and/or take different depolarization routes are known as multifocal PVCs. The treatment for unifocal PVCs may be different than the treatment for multifocal PVCs.

However, because the number of PVCs occurring within a given day may number in the hundreds or thousands, it is currently not feasible for a technician to review the amount of data required to deduce whether the PVC is unifocal or multifocal. In addition, because the occurrence of PVCs does not typically cause great discomfort to a patient, the occurrences may go unreported. However, long-term PVC prevalence may either cause or be a leading indicator of more serious cardiac conditions. Therefore, it would be beneficial to not only detect and monitor the prevalence of PVC in a patient, but further determine the type/cause of the PVCs, such that appropriate treatment may be applied.

SUMMARY

According to an exemplary embodiment, a method of monitoring and reporting premature ventricular contractions (PVCs) detected in a patient is provided. The method includes monitoring an electro-cardiogram (ECG) signal of the patient with an adherent device that includes a plurality of electrodes. Premature ventricular contraction (PVC) beats are detected based on the monitored ECG signal, and ECG episodes associated with detected PVC beats are stored for subsequent analysis. A morphology signal is calculated by quantifying the stored ECG episodes associated with detected PVC beats. Based on the calculated morphology signals, PVC beats are numerically clustered to group PVC beats with similar morphologies together. An output is then generated that includes one or more of a total number of clusters generated, a count of the number of PVC beats included in each cluster, and a representative PVC beat from each cluster.

Another exemplary embodiment of the present invention includes a system for monitoring and reporting premature ventricular contractions (PVCs) detected with respect to a patient. The system includes an adherent device and a processing module. The adherent device includes a plurality of electrodes and sensing circuitry for monitoring an electrocardiogram (ECG) signal of a patient to which the adherent device is affixed. The processing module is configured to receive the monitored ECG signal and detect premature ventricular contraction (PVC) beats based on the monitored ECG signal. In addition, the processing module calculates a morphology signal for each detected PVC beat and numerically clusters the PVC beats based on a comparison of the morphology signals. The processing module then generates an output indicating a total number of clusters generated, a count of the number of PVC beats included in each cluster, and a representative PVC beat from each cluster.

DETAILED DESCRIPTION

The present invention is related to a system and method of monitoring, detecting and diagnosing premature ventricular contractions (PVCs). In particular, the present invention provides system and method of differentiating between unifocal and multifocal PVCs based on the morphology of the detected PVC events, wherein diagnosing the PVCs as unifocal or multifocal allows for different treatments to be selected.

Figure 1:
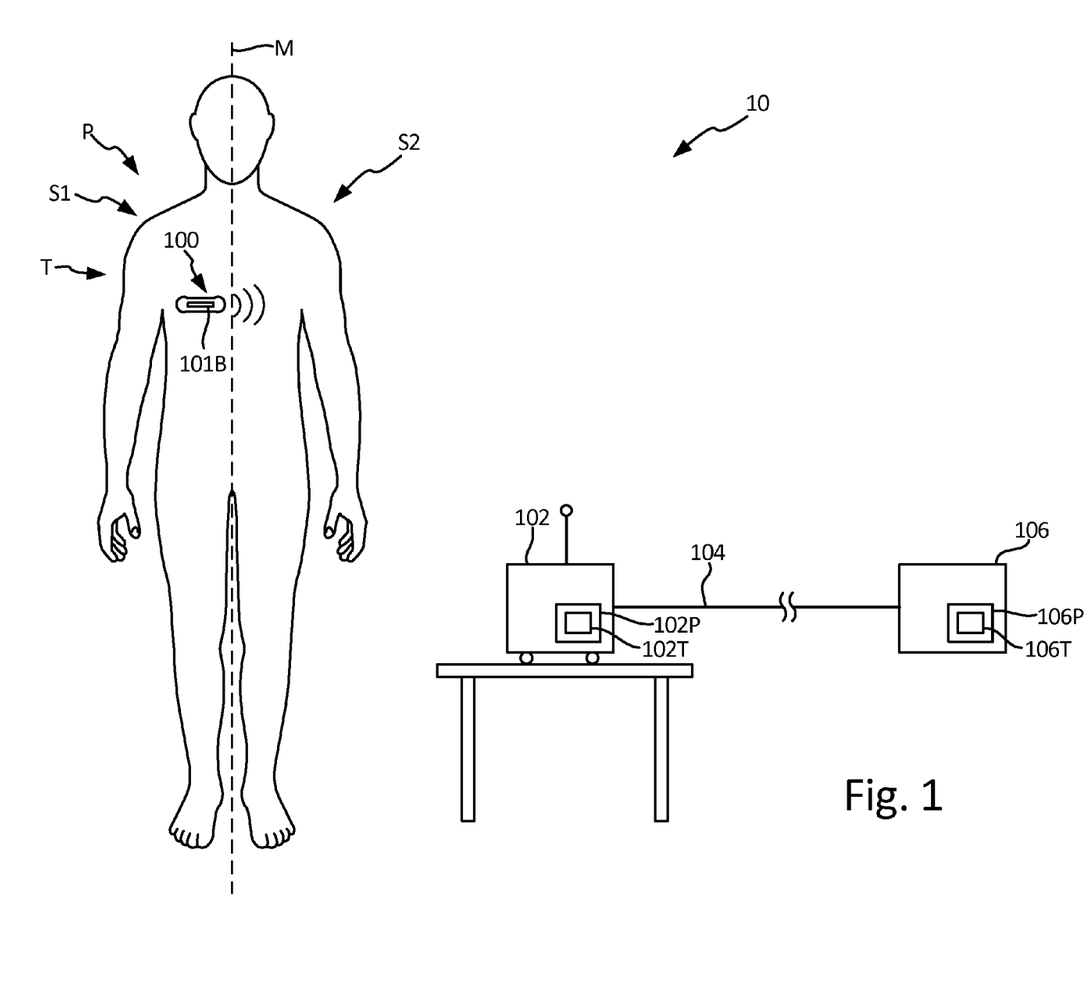
FIG. 1 illustrates a schematic view of a monitoring and treatment system comprising a patient utilizing a medical device capable of long-term monitoring of electrocardiogram (ECG) signals according to an embodiment of the present invention.

FIG. 1 shows a patient P and a monitoring system 10. Patient P comprises a midline M, a first side S1, for example a right side, and a second side S2, for example a left side. Monitoring system 10 comprises a patient measurement device 100, gateway 102, and remote monitoring center 106. In the embodiment shown in FIG. 1, patient measurement device 100 (hereinafter, "adherent device 100") is an adherent device that attaches to the skin of the patient, but in other embodiments may be an implantable or injectable device. Adherent device 100 can be adhered to a patient P at many locations, for example thorax T of patient P. In many embodiments, the adherent device may adhere to one side of the patient, from which side data can be collected. A benefit of utilizing an adherent device such as adherent device 100 is that it may be utilized to collect physiological data from the patient while the patient goes about normal day-to-day activities outside of a hospital setting. This is particularly important in PVC monitoring, in which it is desirable to monitor the occurrence of PVCs over a period of days/weeks and under a variety of circumstances such as at rest, during activity, etc.

Adherent device 100 is capable of monitoring a variety of different types of data, including one or more of electrocardiogram signals (ECG), bio-impedance, respiration, heart rate, heart rhythm, heart rate variability (HRV), heart rate turbulence (HRT), heart sounds, respiratory sounds, blood pressure, activity (e.g., rest, active), posture, and wake/sleep. In one embodiment, ECG signals are utilized to automatically detect premature ventricular contractions (PVCs). Detection may occur locally on adherent device 100, with detected PVC events resulting in the corresponding ECG signal being stored for subsequent analysis—either locally or at remote monitoring center 106. The morphology of stored ECG samples corresponding to detected PVC events are analyzed and clustered (i.e., grouped) based on the detected morphology. The clustered morphologies are utilized to determine whether the PVC events are unifocal or multifocal, with treatment being selected based, in part, on this determination.

Adherent device 100 can wirelessly communicate with remote center 106. The communication may occur directly (via a cellular or Wi-Fi network), or indirectly through intermediate device or gateway 102. As described above, in one embodiment ECG signals monitored by adherent device 100 are communicated in their entirety to remote center 106 for analysis. In other embodiments, adherent device 100 locally provides some level of analysis with respect to monitored ECG signals. For example, as described previously, in one embodiment adherent device 100 monitors ECG signals and through local processing detects the presence of PVC beats. The ECG signal associated with the detected PVC beat is stored (e.g., capture of a 300-400 millisecond window associated with the detected PVC beat) and communicated to remote enter 106 for subsequent morphology analysis and clustering.

The gateway 102 may comprise components of the zLink™, a small portable device similar to a cell phone that wirelessly transmits information received from adherent device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by expert human operators to verify accuracy. For example, ECG samples (i.e., strips) captured and communicated to remote center 106 from adherent device 100 are analyzed based on the morphology associated with each ECG sample and clustered with ECG samples having similar morphologies. Once clustered according to detected ECG morphology, a representative ECG sample from each cluster may be provided to a human expert for review and feedback, which may include verification of the morphology analysis conducted as a well as additional input regarding further clustering of similar ECG samples.

In an exemplary embodiment, monitoring system 10 comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including ECG samples—monitored by adherent device 100 may be analyzed by one or more of the distributed processors included as part of adherent device 100, gateway 102, and/or remote monitoring center 106.

In an exemplary embodiment, adherent device 100 may continuously monitor physiological parameters, communicate wirelessly with a remote center, and provide alerts when necessary. The adherent patch may attach to the patient's thorax and contains sensing electrodes, battery, memory, logic, and wireless communication capabilities. In an embodiment described in more detail with respect to FIG. 2, adherent device 100 collects physiological data from the patient that includes ECG data. The collected data may be analyzed locally, or communicated to remote center 106 for subsequent analysis, which includes detecting PVCs within the monitored ECG data, and quantifying the morphology associated with each detected PVC event. Morphologies are compared with one another in an effort to group PVC events that share a similar morphology. In one embodiment, based on the clustering of ECG signals associated with PVC events, reports are generated for review by an expert that illustrate the clustering of various detected morphologies and allow the expert to provide feedback. The resulting analysis allows treatment determinations to be made based on a determination of whether the PVC beats are unifocal or multifocal.

Figure 2:
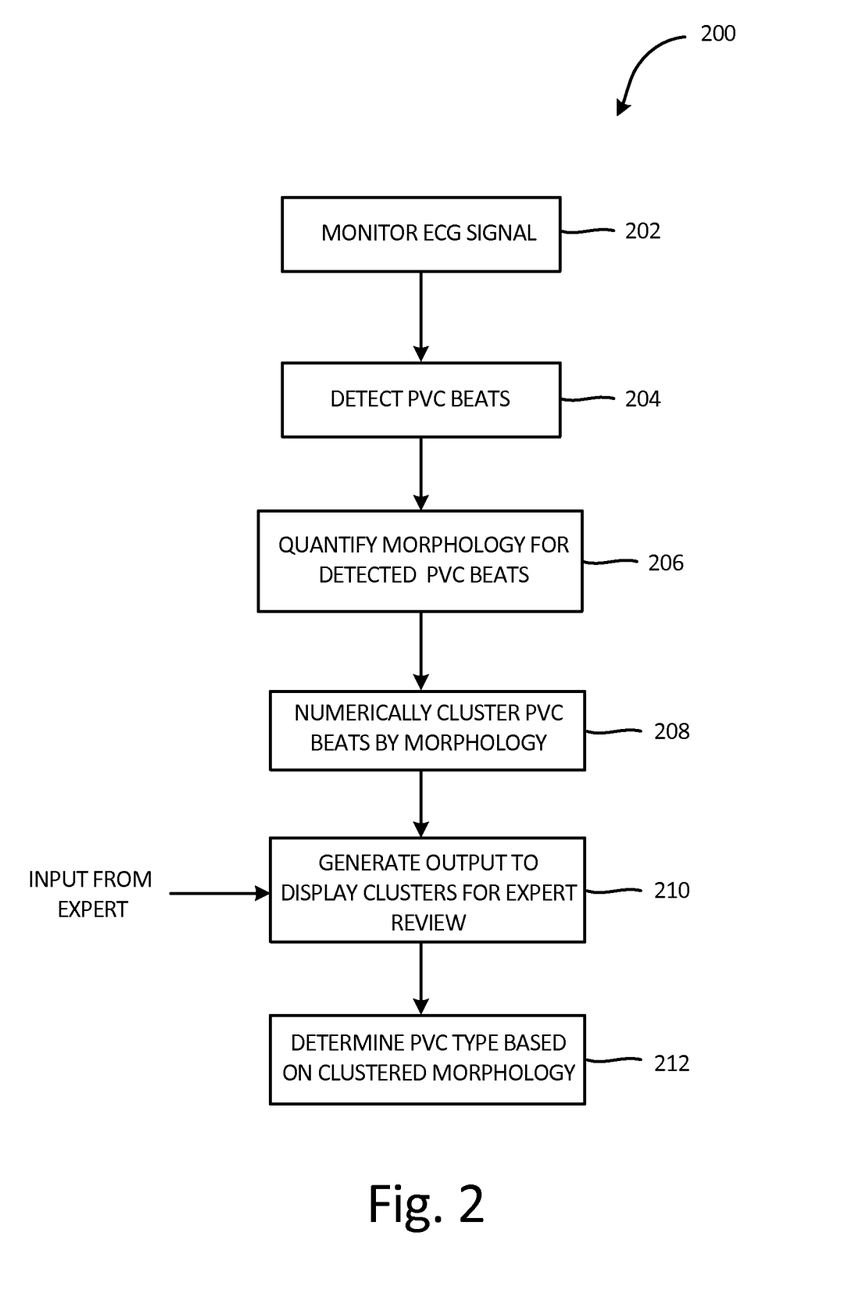
FIG. 2 is a flowchart that illustrates steps performed to detect and classify premature ventricular contractions (PVCs) based on PVC morphology according to an embodiment of the present invention.

FIG. 2 is a flowchart that illustrates a method 200 of monitoring, detecting, diagnosing and reporting premature ventricular contraction (PVC) incidents according to an embodiment of the present invention. At step 202, adherent device 100 monitors an electrocardiogram (ECG) signal associated with the patient. As described with respect to FIG. 1, monitoring may be provided via an adherent device such as the SEEQ continuous monitoring system provided by Medtronic Monitoring Inc. Monitored ECG signals may be stored locally by the adherent device 100 for local processing or may be transmitted—either continuously or intermittently—to remote monitoring center 106 (described with respect to FIG. 1).

At step 204, premature ventricular contractions (PVC) beats are detected based on the monitored ECG signals. In one embodiment, all monitored ECG data is communicated to remote monitoring center 106 for processing of the monitored data. However, in other embodiments, PVC detection may be provided locally by adherent device 100, with only the ECG data associated with detected PVC beats being communicated to remote monitoring center 106 for subsequent processing/analysis. Detection of PVC beats may be provided via any number of well-known detection algorithms. For example, PVC beats may be detected based on QRS-width analysis, frequency-domain analysis, wavelet analysis, artificial neural networks, principal components analysis, as well as combinations thereof.

At step 206, the morphology or shape of detected PVC beats are quantified in a way that allows the morphologies to be compared to one another numerically. Once again, processing of detected PVC beats may be performed locally by adherent device 100 or remotely via remote monitoring center 106. A benefit of quantifying the morphology of the detected PVC beats at remote monitoring center 106 is the conservation of battery power available to adherent device 100.

A variety of methods may be employed to quantify the shape or morphology of the detected PVC beats. In one embodiment, a wavelet signal transform is applied to the ECG signal corresponding to a detected PVC beat. The wavelet signal decomposition of the ECG signal is selected to allow the shape of the PVC beat to be analyzed without noise and non-relevant ECG components (e.g., U-waves). That is, analysis is limited to the components of the ECG signal used to detect PVC beats and identify the shape of the PVC beat. In addition, utilizing wavelet signal decomposition allows for localizing interesting QRS features both in time (i.e., when they occur) and frequency (i.e., shape). For example, in one embodiment the morphology signal $s_{morph}$ is formed as a linear combination of sub-band signals defined as follows:

$$s_{morph} = y_{bph} + y_{bpm} + y_{bpl}$$

wherein $y_{bph}$, $y_{bpm}$, and $y_{bpl}$ are band-pass limited sub-bands that correspond to different frequencies. Various frequency bands may be selected based on requirements and likely noise sources. For example, in one embodiment $y_{bph}$ is equal to a frequency range of between 16 Hz and 40 Hz, $y_{bpm}$ is equal to a frequency range of between 7.3 Hz and 17.8 Hz, and $y_{bpl}$ is equal to a frequency range of between 3.5 Hz and 8.6 Hz. These band-pass ranges are exemplary, but are meant to correspond to high and low frequency ECG components utilized to detect PVC beats. In the example provided, the $y_{bph}$ sub-band is selected to correspond with the high-frequency QRS complex of the ECG signal. The $y_{bpl}$ sub-band is selected to correspond with the P-wave and T-wave components of the ECG signal, and the $y_{bpm}$ sub-band is selected to correspond with some of the T-wave components. In addition, these sub-bands are selected to correspond with frequencies associated with PVC beats and variants in the ECG signal like R-on-T, and further selected to minimize the effects of noise that occur at frequencies outside of the sub-bands. For example, respiratory noise occurs at lower frequencies and can be filtered by selecting the sub-bands having frequencies that exclude the range of frequencies that may include respiratory noise.

In one embodiment, the morphology signal $s_{morph}$ is delayed to align the signal with the peak of the QRS signal. The result of the wavelet signal decomposition, referred to herein as the beat morphology complex $s_{morph}$ represent a numerical representation of the shape of the detected PVC beat. As described in more detail with respect to FIGS. 3a-3b, beat morphology complex $s_{morph}$ can be represented as a feature vector, which is an n-dimensional vector of numerical features that represent the geometry or shape of the QRS complex associated with the PVC beat. For example, in one embodiment each PVC beat is represented as a 64-sample vector. In this way, the morphology or shape of detected PVC beat is quantified for subsequent numerical analysis. In other embodiments, other means of characterizing the PVC beat may be utilized, such as measuring the QRS width of the PVC beat.

In one embodiment, additional steps may be taken when quantifying the PVC beats to account for the possibility that PVCs detected at different heart rates—even unifocal PVCs sharing the same morphology—may result in morphologies that appear different during numerical analysis. That is, a PVC event detected when the patient has a heart rate of 45 beats-per-minute (BPM) may have a different morphology than a PVC beat measured when the patient has a heart rate of 90 BPM, even if the PVC beat originated from the same ectopic location or focus. In one embodiment, prior to or as part of the quantifying of the PVC beats, the samples are scaled to a reference heart rate (e.g., 60 BPM). That is, a common or reference heart rate is selected (e.g., 60 beats per minute), and PVC beats are either contracted or dilated in order to scale the PVC beat to the reference heart rate. For example, a PVC beat occurring at a heart rate of 45 bpm is contracted (i.e., resampled by a factor which is a function of the underlying heart rate and the common reference heart rate) such that the PVC beat is scaled to 60 bpm. Likewise, a PVC beat occurring at a heart rate of 90 bpm is dilated (i.e., resampled by a factor which is a function of the underlying heart rate and the common reference heart rate) such that the PVC beat is scaled to 60 bpm. Subsequent steps are then performed on the scaled PVC beats, quantified as described previously.

At step 208, quantified PVC beats are clustered (i.e., organized into groups) based on the quantified morphology of each PVC beat, such that each cluster includes beats having a shared or similar morphology. In one embodiment, numerical feature vectors are utilized to cluster PVC beats according to morphology. For example, in one embodiment, K-means clustering identifies PVC beats of similar shape/morphology based on a metric calculated with respect to two or more PVC beats. For example, metrics used to cluster beats include correlation metric and distance metric. The correlation distance metric quantifies the similarity in shape between different PVC morphology complexes to allow similar ones to be grouped together. In this way, the output of the clustering of PVC beats is a histogram comprised of a number of a bins or groups, each representing a particular PVC morphology or shape. The number of bins or groups may be determined by a threshold value (e.g., threshold correlation distance in the case of K-means clustering), or may be predetermined to a maximum number of allowable bins. Although other clustering means may be utilized, a benefit of utilizing the K-means cluster is for PVC beats characterized as a vector, K-means clustering provides appropriate clustering. In other embodiments, in which PVC beats are not characterized as vectors, but rather characterized based on features such as QRS width, other types of clustering algorithms may be more appropriate.

At step 210, a report is generated for review by an expert (e.g., medical technician, nurse, doctor) that describes the prevalence of PVC beats by morphology. For example, the report may provide information on total number of PVC beats detected, a breakdown of the number of clusters generated with the respect to the detected PVC beats, the number of PVC beats classified into each of the clusters or bins, and representative samples of the ECG signal corresponding to PVC beats associated with each cluster or bin. The report may provide the information in graphical form, as described below with respect to FIGS. 4a-5c, and may include representative ECG signals corresponding to PVC beats to allow the expert to determine whether PVC beats classified into different clusters or bins should be combined with one another. That is, as illustrated in FIG. 2, the expert is allowed to provide input at step 210 with respect to the data presented. Input provided by the expert may include acquiescence of the clusters formed at step 208, and merging of two or more clusters into a single cluster.

In addition to information regarding the clustering of PVC beats, additional information may be included in the generated report, including PVC burden (e.g., total number of PVC beats, ratio of PVC beats to regular beats, etc.). This information is used to supplement the morphology/clustering data provided as part of the generated report.

In one embodiment, at step 210 an expert reviews the generated report and provides input regarding the created clusters, either acquiescing to the assigned clusters or providing input to combine groups of clusters. In this way, the generated report may be modified based on expert input. However, in other embodiments the reports may be generated without input from an expert.

At step 212, a determination is made whether the collected data indicates that the PVCs are unifocal or multifocal. In one embodiment, the report generated at step 210 provides a diagnosis of the PVCs as either unifocal or multifocal. However, in other embodiments an expert may acquiesce to the diagnosis or may provide input modifying the diagnosis. Treatment is then suggested and/or provided based on the diagnosis. For example, if the report indicates that the PVC is unifocal in nature then treatment may include ventricular ablation. Conversely if the report indicates that the PVC is multifocal then treatment may include use of anti-arrhythmic drugs.

Figure 3A:
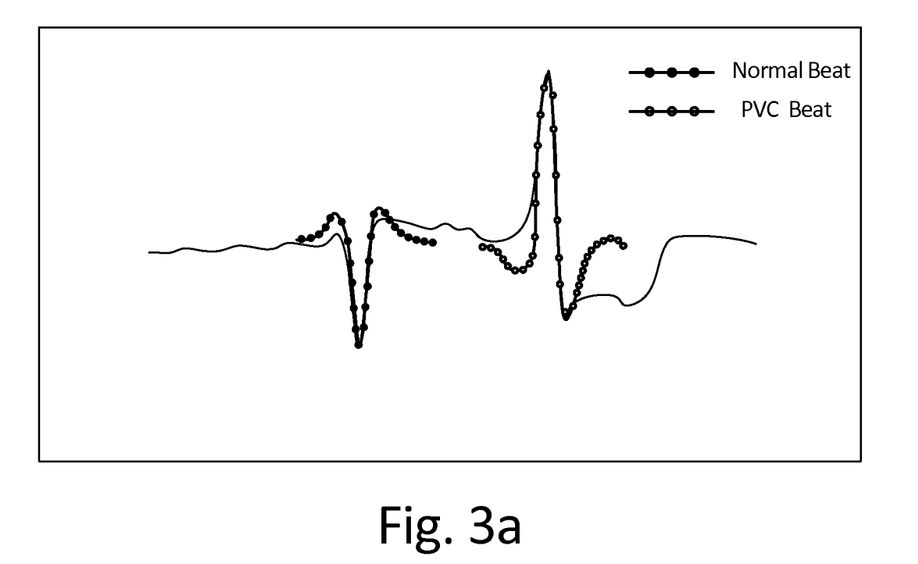
FIGS. 3a and 3b are exemplary ECG signals measured with respect to a patient that each illustrate a detected normal QRS beat followed by a PVC beat with calculated morphology complexes overlayed on top of the ECG signals according to an embodiment of the present invention.
Figure 3B:
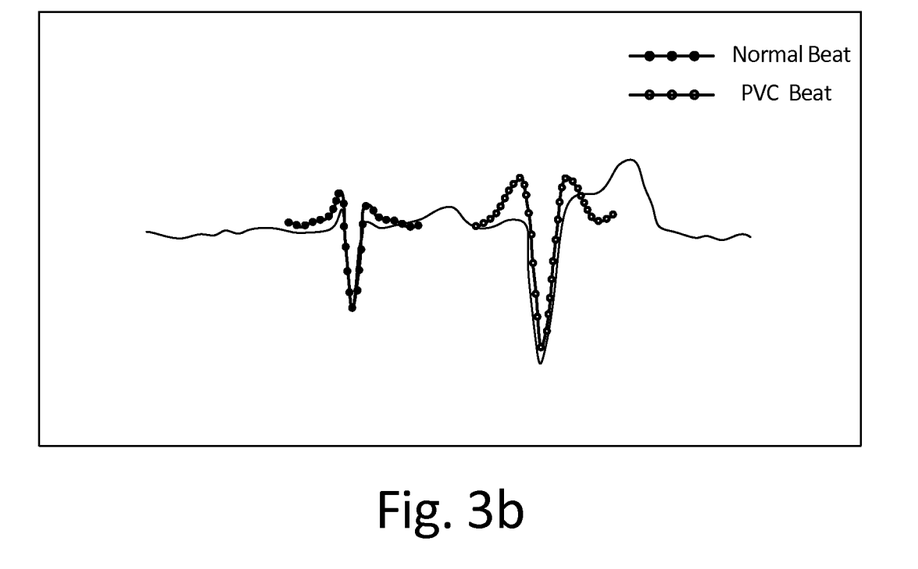

FIGS. 3a and 3b illustrate sample ECG signals measured with respect to a patient that illustrates a detected normal heart beat followed by a PVC beat with calculated morphology complexes overlayed on top of the ECG signals according to an embodiment of the present invention. Monitored ECG signals are illustrated as a solid black line, while solid dots and circles represent the quantification of the ECG signals into morphology signal $s_{morph}$ (described with respect to FIG. 2). In particular, solid dots are illustrated with respect to the normal heart beat, while circles are illustrated with respect to the PVC beat. In the embodiment shown in FIGS. 3a-3b, the morphology signal is generated based on a 320 millisecond (msec) window centered on a detected beat.

As described with respect to FIG. 2, in one embodiment the morphology signal is derived from a wavelet signal decomposition of the ECG that corresponds with the QRS shape without noise/P-wave/T-wave components. This is illustrated visually in FIG. 3a, in which with respect to both the normal heart beat and the PVC beat the P-wave component (triggered prior to the QRS complex) and T-wave component (triggered after the QRS complex) are effectively filtered, along with noise. Because the resulting morphology signal $s_{morph}$ shown in FIGS. 3a and 3b is quantized (for example, as feature vectors), the morphology signal $s_{morph}$ can be compared to other morphology signals and clustered according to a numerical comparison.

The embodiment shown in FIG. 3b illustrates another example of a normal heart beat followed by a PVC beat. Notice that the morphology of the PVC beat illustrated in FIG. 3b is different from that shown in FIG. 3a, and thus subsequent clustering of the PVC beat shown in FIGS. 3a and 3b would result in the PVC beats being placed into different clusters. The difference in morphology indicates that the PVC beats originated at different ectopic locations, and that the patient's PVC condition is multifocal rather than unifocal.

Figure 4A:
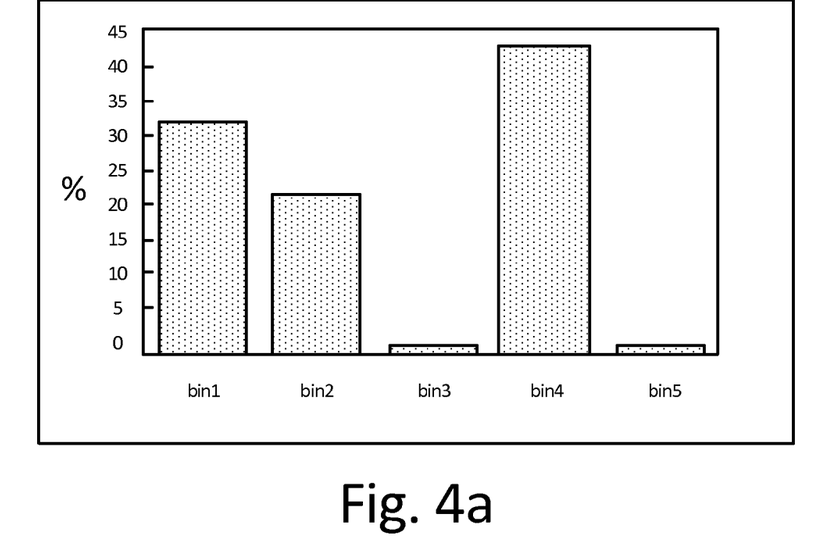
FIG. 4a is a histogram chart that illustrates grouping of detected PVC beats by morphology into a plurality of bins/clusters according to an embodiment of the present invention.

FIG. 4a is a histogram chart that illustrates grouping of detected PVC beats by morphology into a plurality of bins (i.e., clusters) according to an embodiment of the present invention. Each of the plurality of bins shown along the x-axis represents different shape morphologies. In the embodiment shown in FIG. 4a, a total of five bins are illustrated, (labeled as bin1, bin2, bin3, bin4 and bin5) representing a total of five different shape morphologies. The y-axis illustrates the percentage of PVC beats placed into each of the respective bins. For example, 42% of detected PVC beats detected were classified as sharing a particular morphology. This means of the plurality of PVC beats detected and quantized, approximately 42% were classified as having a shape/morphology that resulted in them being clustered together. Similarly, 32% of detected PVC beats were classified in bin1, 22% of detected PVC beats were classified in bin2, 3% of detected PVC beats were classified in bin3, and 1% of detected PVC beats were classified in bin5. However, with the number of beats classified as sharing different morphologies, initial diagnosis indicates multifocal PVC.

The number of bins utilized may be pre-defined or defined at the time of clustering. In one embodiment described with respect to FIG. 2, above, clusters are created via a correlation distance metric that quantifies the similarly in shape between different PVC morphologies. A threshold correlation distance metric is defined to determine whether a particular PVC morphology is similar enough to other PVC morphologies to group together. By varying the threshold correlation distance metric, the number of bins created may be dynamically modified.

Figure 4B:
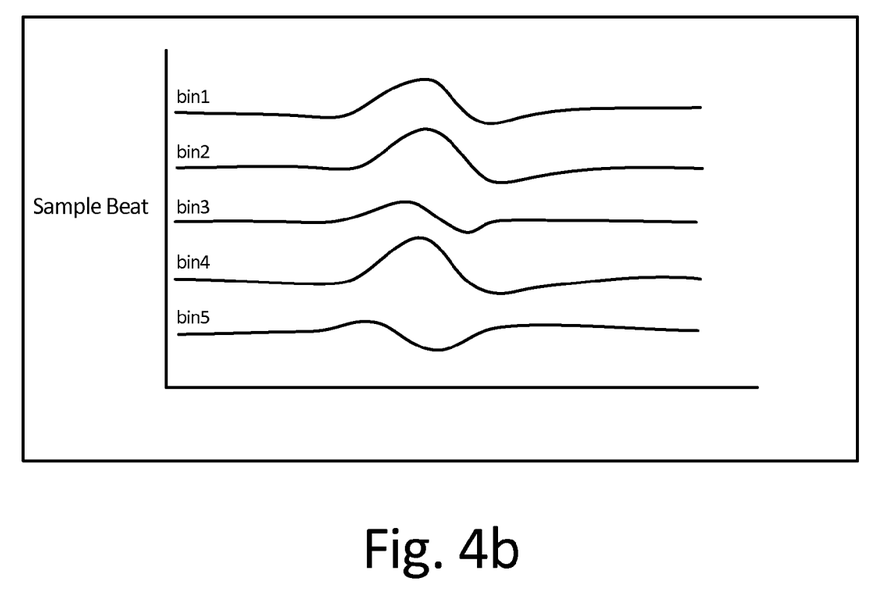
FIG. 4b is a report generated by selecting a representative ECG sample from each bin described with respect to FIG. 4a to illustrate visually differences in ECG morphology between each bin according to an embodiment of the present invention.
Figure 4C:
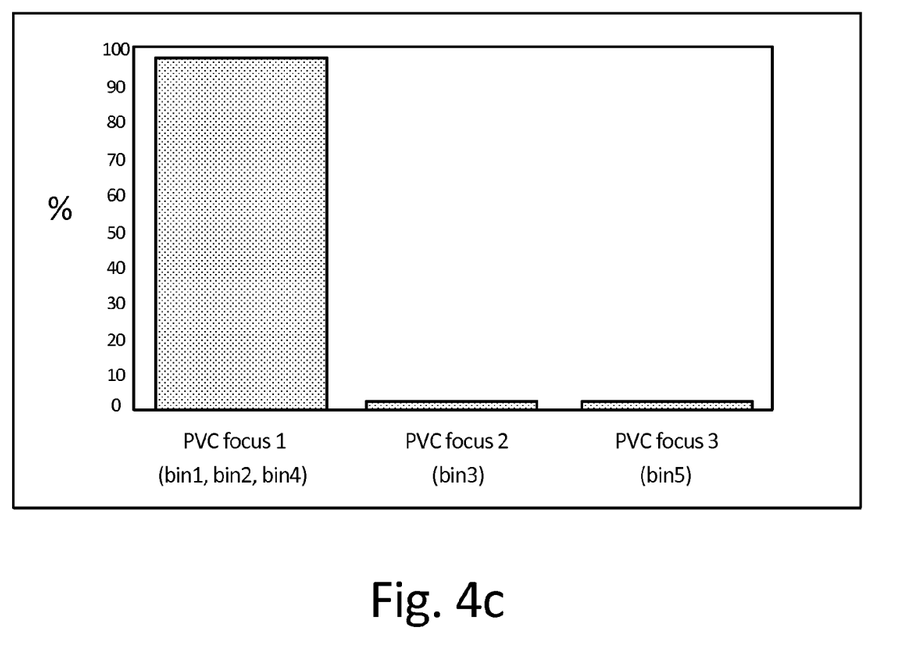
FIG. 4c is a histogram chart illustrates the incorporation of expert input to modify the bins/clusters shown in FIG. 4a according to an embodiment of the present invention.

FIG. 4b is a report generated by selecting a representative ECG sample from each bin described with, respect to FIG. 4a, the representation ECG sample allow an expert user to visually review the general morphology/shape of each cluster of detected PVC beats. The example report shown in FIG. 4b corresponds with the exemplary report described with respect to FIG. 4a, in which PVC beats were grouped into five clusters labeled bin1, bin2, bin3, bin4, and bin5. For each of the five clusters, a representative ECG sample is presented for review by an expert. Thus, a representative ECG sample is provided with respect to cluster bin1, while another representative ECG sample is provided with respect to cluster bin2, and so on. In addition to providing the expert with a visual representation of the morphology of the various PVC beats, the expert can review and determine whether two or more of the clusters share a morphology that dictates combining the clusters together. For example, in the embodiment shown in FIG. 4b, the representative ECG sample associated with clusters bin1, bin2, and bin3 share a similar morphology that is fairly easy to discern visually. As a result, the expert may respond with instructions to combine the PVC beats organized into clusters bin1, bin2, and bin3. Ideally, the PVC beats organized into bin1, bin2, and bin3 would have been originally placed into one cluster. However, in the event that the clustering algorithm generates different clusters, provision of an ECG sample representative of the PVC morphology of each cluster allows an expert to correct the classification. In the instant example, input from an expert to combine bin1, bin2, and bin4 results in three remaining bins of PVC beats having different morphologies. However, per the information provided in FIG. 4a, as a result of the combination of clusters bin1, bin2, and bin4, the resulting combined bin will include approximately 95% of detected PVC beats (as shown in FIG. 4c, which illustrates the distribution of PVC beats as a result of this combination). The modification may result in the PVCs being identified as unifocal rather than multifocal, although at least several PVC beats were detected that likely originate form a different ectopic location.

Figure 5A:
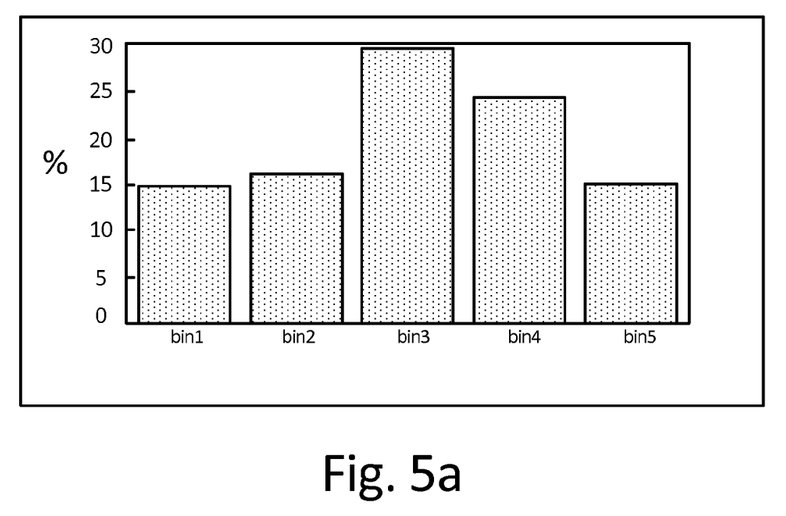
FIG. 5a is a histogram chart that illustrates grouping of detected PVC beats by morphology into a plurality of bins according to another embodiment of the present invention.
Figure 5B:
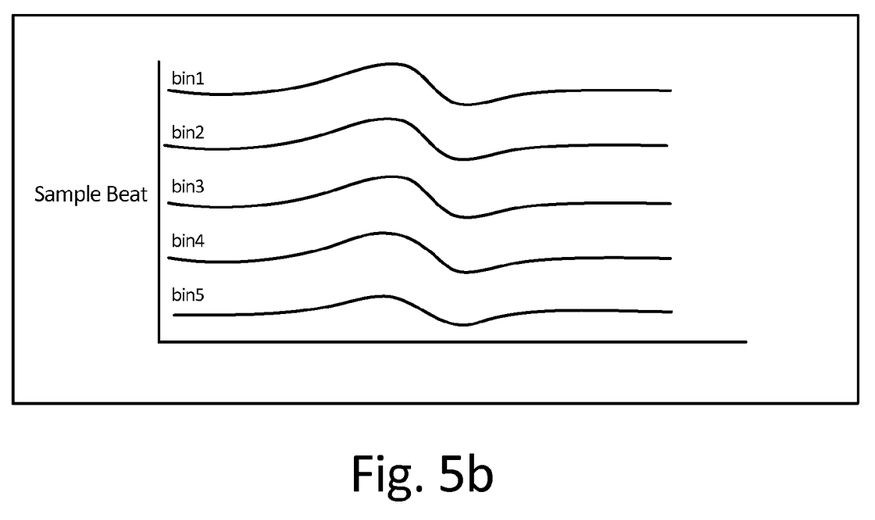
FIG. 5b is a report generated by selecting a representative ECG sample from each bin described with respect to FIG. 5a to illustrate differences in ECG morphology according to another embodiment of the present invention.
Figure 5C:
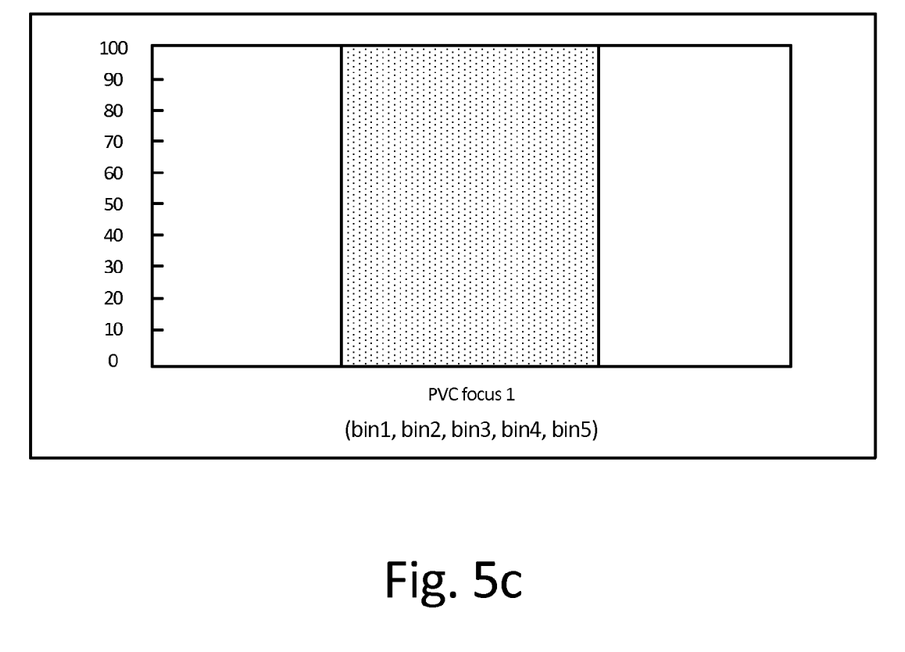
FIG. 5c is a histogram chart that illustrates the incorporation of expert input to modify the bins/clusters shown in FIG. 4a according to an embodiment of the present invention.

FIGS. 5a-5c illustrate another exemplary set of reports generated according to an embodiment of the present invention. Once again, FIG. 5a a histogram chart that illustrates grouping of detected PVC beats by morphology into a plurality of clusters or bins; FIG. 5b illustrates a representative ECG sample, and FIG. 5c illustrates a histogram chart that illustrates grouping of detected PVC beats after an expert has provided input.

In the histogram shown in FIG. 5a, PVC beats have been organized according to morphology into five different bins. The distribution of PVC beats organized into the bins is fairly even as illustrated in FIG. 5a, with approximately 15% of PVC beats located in bin1, bin2, and bin5, approximately 30% located in bin3, and approximately 25% located in bin4. The representative ECG samples illustrated in FIG. 5b, however, indicate that the morphology of the PVC beats located in each of the plurality of bins are similar to one another. As a result, the expert may provide input that bins bin1-bin5 should be combined. As a result, all detected PVC beats are combined into a single bin, as indicated in FIG. 5c.

Figure 6:
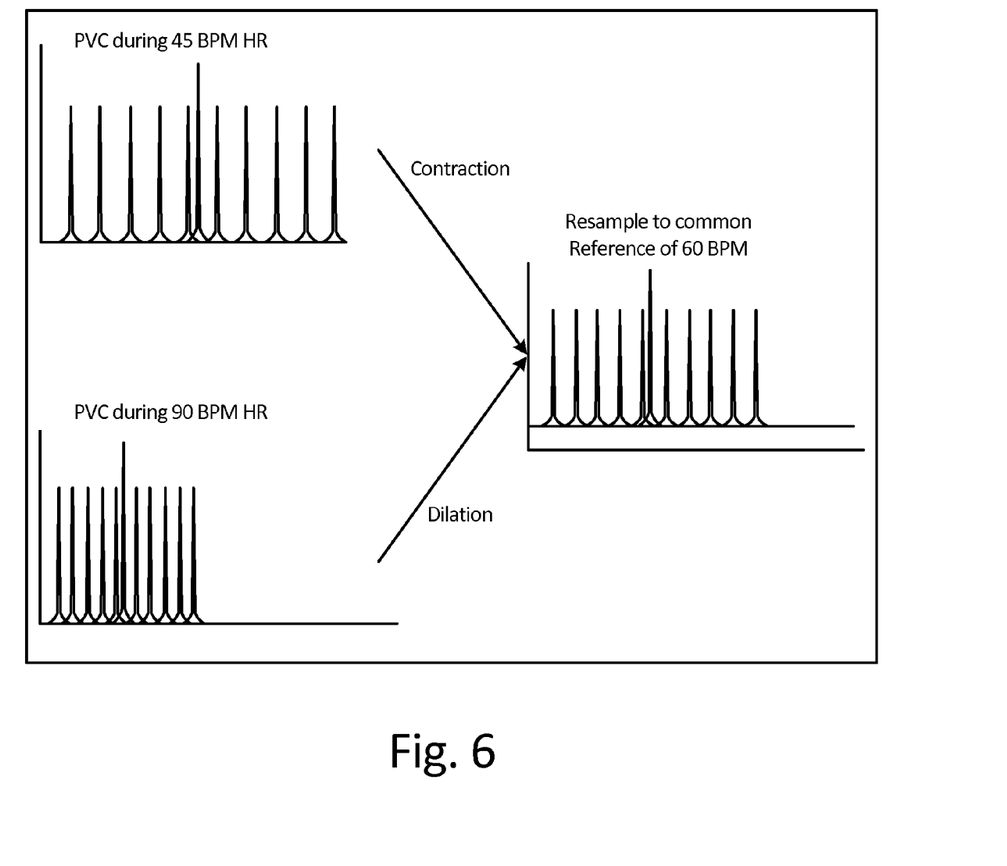
FIG. 6 illustrates the scaling ECG signals to a common reference heart rate via selective contraction/dilation of the ECG signals according to an embodiment of the present invention.

FIG. 6 illustrates a method of contracting/dilating ECG signals to a common reference heart rate as part of the quantifying process according to an embodiment of the present invention. As described with respect to FIG. 2, when quantifying the morphology of detected PVC beats, the quantification may be carried out directly on ECG samples corresponding with detected PVCs, or may be modified first to account for variations in the underlying heartrate of the patient. FIG. 6 illustrates how the underlying ECG signal can be contracted and/or dilated to scale the ECG signal to a reference heart rate. A benefit of contracting/dilating the underlying ECG sample is that PVCs starting from the same ectopic location may appear to have a different morphology due to differences in the underlying heartbeat. Contracting/dilating the ECG samples to a reference heart rate ensures that PVCs originating from the same ectopic location share the same morphology for analysis purposes regardless of heart rate.

For example, in the top portion of FIG. 6, a PVC beat is detected with an underlying heart rate of 30 beats-per-minute (BPM). If the selected reference heart rate is 60 BPM, then the ECG sample monitored at 30 BPM must be contracted by a factor of two in order to properly scale the ECG sample. Conversely, as illustrated in the bottom portion of FIG. 6, a PVC beat is detected with an underlying heart rate of 120 beats-per-minute (BPM), the ECG sample must be dilated by a factor of two in order to properly scale the ECG sample to 60 BPM.

Thus, contracting/dilating ECG signals requires a reference heart rate to be selected, and then for each ECG sample analyzed, information regarding the underlying heart rate of the sample must be known. Based on the reference heart rate and the sample heart rate, a multiplier factor is selected to provide the desired contraction/dilation of the underlying ECG sample. A benefit of this approach is that scaling the underlying ECG signals improves the ability to cluster similarly shaped PVCs occurring at different underlying heartrates.

Figure 7A:
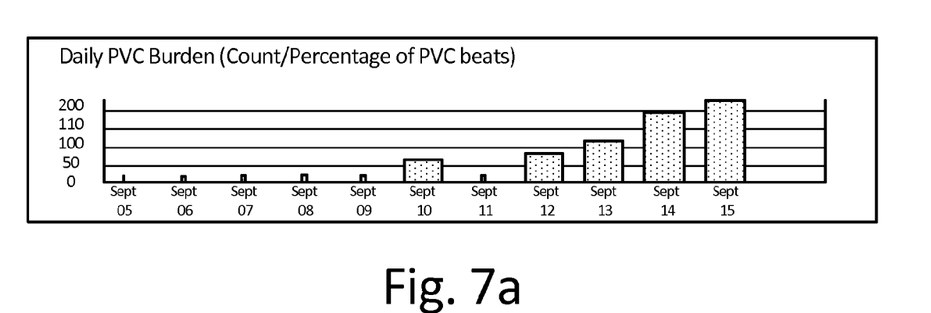
FIGS. 7a-7c are charts that illustrate monitoring/reporting of detected PVC events according to an embodiment of the present invention.
Figure 7B:
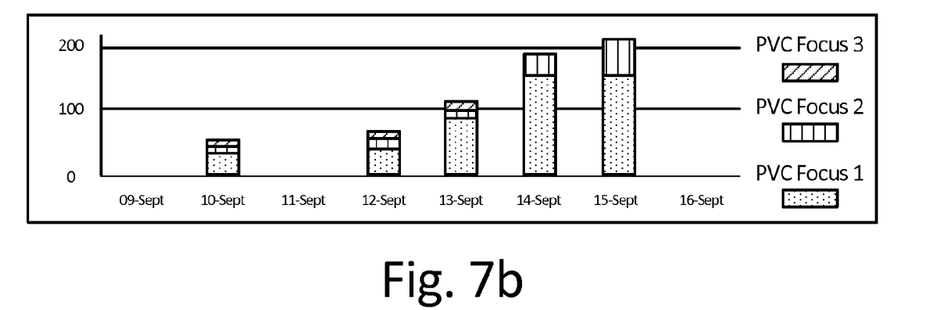
Figure 7C:
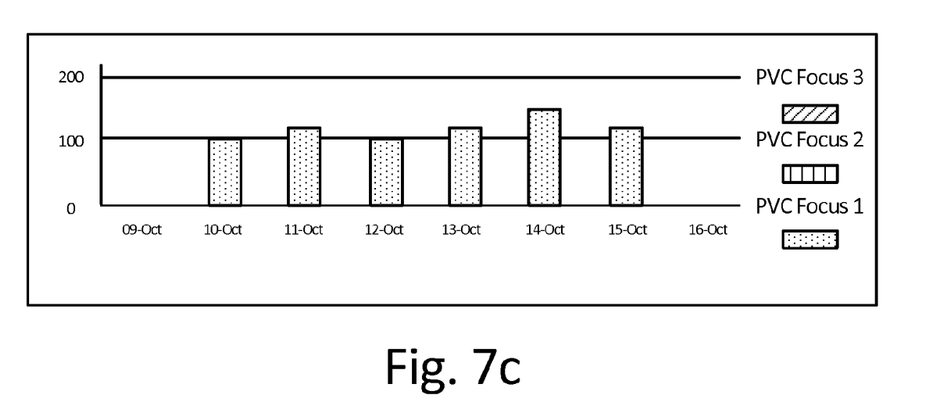

FIGS. 7a-7c are examples of the types of reports/charts that may be generated and provided to an expert for review according to an embodiment of the present invention. FIG. 7a is a chart that illustrates the PVC burden monitored over a 12-day period. The PVC burden is a representation of the total number of PVC events detected in a given day. In the embodiment shown in FIG. 7a, it is represented both as a total count of PVC beats detected, and as a percentage of total beats monitored in a day. For example, on September 10, a total of fifty-seven PVC beats were detected, which was approximately 0.1% of all beats monitored in a day. On September 15, a total of approximately two-hundred PVC beats were detected, which was approximately 0.3% of all beats detected.

FIGS. 7b and 7c are charts that provide additional information regarding the PVC beats detected according to an embodiment of the present invention. In particular, in addition to providing a count of the total number of PVC beats detected, the charts shown in FIGS. 7b and 7c represent the morphology of the PVC beats detected. For example, in the embodiment shown in FIG. 7b, a total of three different clusters or groups of PVC beats have been detected. For example, the entry corresponding to September $10^{th}$ indicates not only that approximately fifty PVC beats were detected, but that PVC beats were detected with respect to three different morphologies organized into three bins. The number of PVCs detected each day continues to rise until September 15, in which PVC events according to two different morphologies were detected. An expert reviewing the information provided in FIG. 7b would be able to quickly assess that the total number of PVC events has been increasing over the past few days, and that the PVC is likely multifocal in nature due to the plurality of different morphologies, pending review of representative morphologies from each bin. In contrast, the chart shown in FIG. 7c indicates that the number of PVC events has remained relatively stable over the past few days, and furthermore that the PVC events detected share a single morphology, indicating that the PVCs are likely unifocal.

Figure 8:
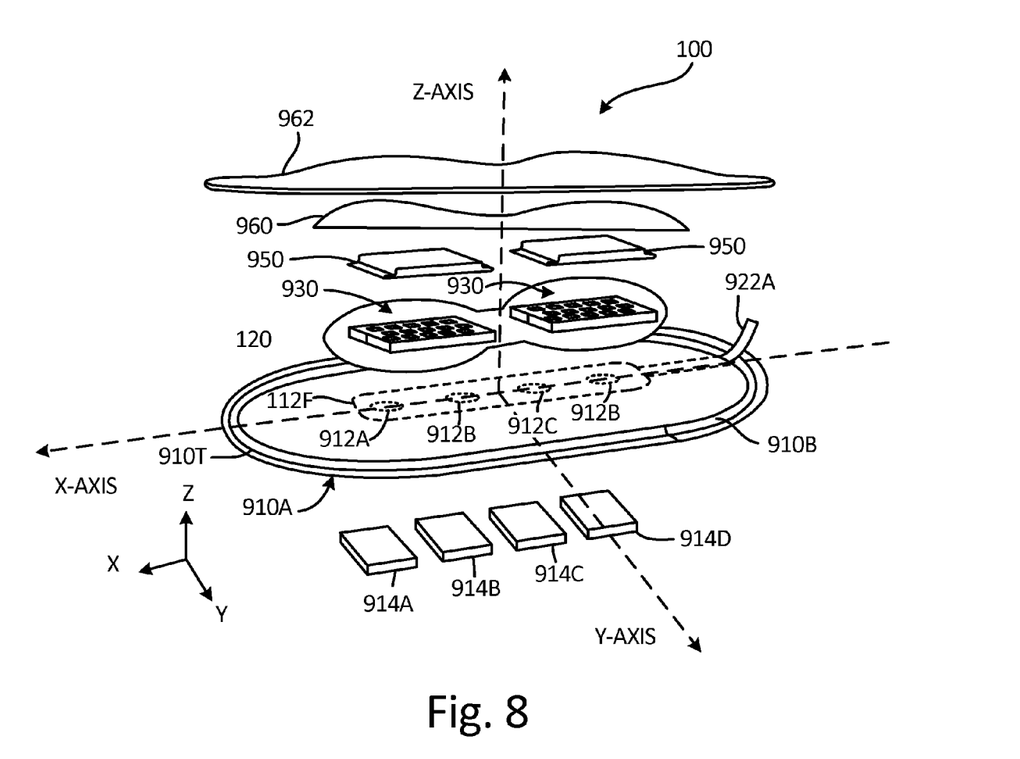
FIG. 8 shows an exploded view of an adherent device according to an embodiment of the present invention.

FIG. 8 is an exploded view, respectively, of embodiments of adherent device 100. In the embodiment shown in FIG. 8, adherent device includes adherent tape 910T, electrodes 912A, 912B, 912C, 912D with gels 914A, 914B, 914C, 914D, printed circuit board (PCB) 920, flexible connected 922A, electrical components/sensors 930 mounted on PCB 920, batteries 950, electronics housing cover 960, and flexible cover 962.

Adherent device 100 comprises at least two electrodes—although the embodiment shown in FIG. 8 includes electrodes 912A, 912B, 912C and 912D. Adherent device 100 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 100 comprises a first side, or a lower side 910A, that is oriented toward the skin of the patient when placed on the patient. The adherent patch 100 may also comprise a tape 910T which is a material, preferably breathable, with an adhesive (not shown) to adhere to patient P. Electrodes 912A, 912B, 912C and 912D are affixed to adherent patch 100. In many embodiments, at least four electrodes are attached to the patch. Gels 914A, 914B, 914C and 914D can each be positioned over electrodes 912A, 912B, 912C and 912D, respectively, to provide electrical conductivity between the electrodes and the skin of the patient. Adherent patch 100 also comprises a second side, or upper side 910B. In many embodiments, electrodes 912A, 912B, 912C and 912D extend from lower side 910A through adherent patch 100 to upper side 910B. An adhesive can be applied to upper side 910B to adhere structures, for example a breathable cover, to the patch such that the patch can support the electronics and other structures when the patch is adhered to the patient. In many embodiments, adherent patch 100 may comprise a layer of breathable tape 910T, for example a tricot-knit polyester fabric, to allow moisture vapor and air to circulate to and from the skin of the patient through the tape. Electrical signals received at electrodes 912A-912D may be communicated to electronic components 930 via flexible connection 922A, which is connected to PCB 920.

In addition, electronic components 930 may include ECG circuitry utilized to generate electrocardiogram signals and data from two or more of electrodes 912A, 912B, 912C and 912D in many ways. In some embodiments, ECG circuitry (not shown) is connected to inner electrodes 912B and 912C, which may comprise sense electrodes of the impedance circuitry as described above. In many embodiments, the ECG circuitry may measure the ECG signal from electrodes 912A and 912D when current is not passed through electrodes 912A and 912D.

In addition, electronic circuitry 930 may comprise a processor module that can be configured to analyze physiological parameters monitored by adherent device 100 and to control collection and transmission of data from the electrocardiogram circuitry. In one embodiment, the processor module included as part of electronic circuitry 930 comprises a tangible medium, for example read only memory (ROM), electrically erasable programmable read only memory (EEPROM) and/or random access memory (RAM). Processing of monitored physiological parameters such as ECG signals may therefore be distributed between the local processor module included as part of electronic circuitry 930 and remote monitoring system 106. For example, processing module may be configured to process monitored ECG signals to detect PVC beats, while quantifying the morphology of the PVC beats and clustering PVC beats based on the quantified morphology may be processed remotely by remote monitoring system 106.

In many embodiments, electronics components 930 comprise wireless communications circuitry (not shown) to communicate with remote center 106. PCB 920 may comprise an antenna to facilitate wireless communication. The antenna may be integral with PCB 920 or may be separately coupled thereto. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two way protocol such that the remote center is capable of issuing commands to control data collection.

In this way, the disclosure provides a system and method of monitoring, detecting and classifying PVC beats based on morphology. A benefit of the present invention is that combined with an adherent device that may be worn over a plurality of days, the present invention may monitor and analyze hundreds of detected PVC beats occurring during a plurality of patient activities. In addition, the present invention provides a method of organizing the hundreds or more of detected PVC beats into meaningful reports that allow an expert user to review the hundreds if not thousands of PVC beats occurring over a period of time to aid in diagnosing the cause of the PVC beats. For example, if all or most of the PVC beats share a common morphology, a determination is made that the PVC beats are unifocal (i.e., originating from the same ectopic location). Conversely, if the report indicates that the PVC beats include two or more morphologies, a determination is made that the PVC beats are multifocal (i.e., originating from two or more ectopic locations). Treatment decisions may be made based on this information.

Discussion of Possible Embodiments

The following are non-exclusive descriptions of possible embodiments of the present invention.

According to an exemplary embodiment, a method of monitoring and reporting premature ventricular contractions (PVCs) detected in a patient is provided. The method includes monitoring an electro-cardiogram (ECG) signal of the patient with an adherent device that includes a plurality of electrodes. In addition, the method includes detecting premature ventricular contraction (PVC) beats based on the monitored ECG signal, and storing ECG episodes associated with detected PVC beats. A morphology signal is calculated by quantifying the stored ECG episodes associated with detected PVC beats, a and PVC beats are then numerically clustered based on the calculated morphology signals to group PVC beats of a similar shape. Finally, an output is generated that includes one or more of a total number of clusters generated, a count of the number of PVC beats included in each cluster, and a representative PVC beat from each cluster.

The method of the preceding paragraph can optionally include, additionally and/or alternatively any, one or more of the following features, configurations and/or additional components.

The step of calculating the morphology signal may further include calculating a wavelet signal decomposition of the ECG episode associated with each detected PVC beat.

The step of calculating the morphology signal may further include calculating a wavelet signal decomposition of the ECG episode associated with each detected PVC beat.

The method may further include wherein calculating the wavelet signal decomposition of the ECG episode includes utilizing a linear combination of sub-band signals defined by equation $s_{morph}$=ybph+ybpm+ybpl, wherein ybph, ybpm, and ybpl are band-pass limited sub-bands that correspond to different QRS frequencies and $s_{morph}$ is the resulting morphology signal.

The step of numerically clustering the PVC beats may further include utilizing a correlation distance metric to compare morphology signals and cluster PVC beats sharing a similar morphology.

The method may further include scaling the calculated morphology signals to a reference heart rate.

The step of scaling the calculated morphology may further include contracting/dilating the calculated morphology based on a heart rate of the PVC beat and a reference heart rate.

In another embodiment, a system monitors and reports premature ventricular contractions (PVCs) detected with respect to a patient. The system includes an adherent device and a processing module. The adherent device may include a plurality of electrodes and sensing circuitry for monitoring an electrocardiogram (ECG) signal of a patient to which the adherent device is affixed. The processing module may be configured to receive the monitored ECG signal, wherein the processing module detects premature ventricular contractions (PVC) beats based on the monitored ECG signal. The processing module may then calculate a morphology signal for each detected PVC beat and numerically cluster the PVC beats based on a comparison of the morphology signals. In addition, the processing module may generate an output indicating a total number of clusters generated, a count of the number of PVC beats included in each cluster, and a representative PVC beat from each cluster.

The system may further include wherein the output generated by the processing module includes an indication of whether the PVC beats are unifocal or multifocal based on numerical clustering of the PVC beats.

The system may further include wherein the processing module utilizes a wavelet signal decomposition to calculate the morphology of each PVC beat.

The system may further include wherein the wavelet signal decomposition of the PVC beat is based on a linear combination of sub-band signals defined by equation $s_{morph} = ybph + ybpm + ybpl$, wherein ybph, ybpm, and ybpl are band-pass limited sub-bands that correspond to different QRS frequencies and $s_{morph}$ is the resulting morphology signal.

The system may further include wherein numerical clustering of PVC beats by the processing module includes calculating a correlation distance metric between two or more PVC beats to determine whether the PVC beats should be included in the same cluster, wherein the calculated correlation distance metric is compared to a threshold value.

The system may further include wherein the processing module provides scaling of the calculated morphology signals to a reference heart rate prior to or as part of calculating a morphology of each PVC beat.

The system may further include wherein the processing module selectively contracts/dilates the calculated morphology based on a determined heart rate of the PVC beat and a reference heart rate.

The processing module may be a distributed processing system that includes a processor located locally on the adherent device and a processor located remotely at a remote monitoring center, wherein the adherent device further includes a wireless transmitter configured to communicate data from the adherent device to the remote monitoring center.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of monitoring and reporting premature ventricular contractions (PVCs) detected in a patient, the method comprising:

monitoring an electro-cardiogram (ECG) signal of the patient with an adherent device that includes a plurality of electrodes;

detecting premature ventricular contraction (PVC) beats based on the monitored ECG signal, and storing ECG episodes associated with detected PVC beats;

calculating a morphology signal by quantifying the stored ECG episodes associated with detected PVC beats;

numerically clustering the PVC beats based on the calculated morphology signals to group PVC beats having a similar morphology;

generating an output that includes one or more of a total number of clusters generated, a count of the number of PVC beats included in each cluster, and a representative PVC beat from each cluster wherein calculating the morphology signal includes calculating a wavelet signal decomposition of the ECG episode associated with each detected PVC beat, and wherein calculating the wavelet signal decomposition of the ECG episode includes utilizing a linear combination of sub-band signals defined by equation $s_{morph} = ybph + ybpm + ybpl$, wherein ybph, ybpm, and ybpl are band-pass limited sub-bands that correspond to different QRS frequencies and $s_{morph}$ is the resulting morphology signal.

2. The method of claim 1, wherein generating an output includes providing an indication of whether the PVC beats are unifocal or multifocal based on numerical clustering of the PVC beats.

3. The method of claim 1, wherein numerically clustering the PVC beats includes utilizing a correlation distance metric to compare morphology signals and cluster PVC beats sharing a similar morphology.

4. The method of claim 1, further including scaling the calculated morphology signals to a reference heart rate.

5. The method of claim 4, wherein scaling includes contracting/dilating the calculated morphology based on a heart rate of the PVC beat and a reference heart rate.

6. A system for monitoring and reporting premature ventricular contractions (PVCs) detected with respect to a patient, the system comprising:

an adherent device that includes a plurality of electrodes and sensing circuitry for monitoring an electrocardiogram (ECG) signal of a patient to which the adherent device is affixed;

a processing module configured to receive the monitored ECG signal, wherein the processing module detects premature ventricular contractions (PVC) beats based on the monitored ECG signal, wherein the processing module calculates a morphology signal for each detected PVC beat and numerically clusters the PVC beats based on a comparison of the morphology signals, wherein the processing module generates an output indicating a total number of clusters generated, a count of the number of PVC beats included in each cluster, and a representative PVC beat from each cluster, wherein the processing module utilizes a wavelet signal decomposition to calculate the morphology of each PVC beat and wherein the wavelet signal decomposition of the PVC beat is based on a linear combination of sub-band signals defined by equation $s_{morph} = ybph + ybpm + ybpl$, wherein ybph, ybpm, and ybpl are band-pass limited sub-bands that correspond to different QRS frequencies and $S_{morph}$ is the resulting morphology signal.

7. The system of claim 6, wherein the output generated by the processing module includes an indication of whether the PVC beats are unifocal or multifocal based on numerical clustering of the PVC beats.

8. The system of claim 6, wherein numerical clustering of PVC beats by the processing module includes calculating a correlation distance metric between two or more PVC beats to determine whether the PVC beats should be included in the same cluster, wherein the calculated correlation distance metric is compared to a threshold value.

9. The system of claim 6, wherein the processing module further provides scaling of the calculated morphology signals to a reference heart rate prior to or as part of calculating a morphology of each PVC beat.

10. The system of claim 9, wherein the processing module selectively contracts/dilates the calculated morphology based on a determined heart rate of the PVC beat and a reference heart rate.

11. The system of claim 6, wherein the processing module is a distributed processing system that includes a processor located locally on the adherent device and a processor located remotely at a remote monitoring center, wherein the adherent device further includes a wireless transmitter configured to communicate data from the adherent device to the remote monitoring center.

12. A method of monitoring and reporting premature ventricular contractions (PVCs) detected in a patient, the method comprising:
 monitoring an electro-cardiogram (ECG) signal of the patient with an adherent device that includes a plurality of electrodes;
 detecting premature ventricular contraction (PVC) beats based on the monitored ECG signal, and storing ECG episodes associated with detected PVC beats;
 determining an underlying heart rate associated with the monitored ECG signal;
 calculating a morphology signal by quantifying the stored ECG episodes associated with detected PVC beats, wherein calculating a morphology signal includes scaling the calculated morphology signals to a reference heart rate based on the determined underlying heart rate;
 numerically clustering the PVC beats based on the calculated morphology signals to group PVC beats having a similar morphology; and
 generating an output that includes one or more of a total number of clusters generated, a count of the number of PVC beats included in each cluster, and a representative PVC beat from each cluster.

13. The method of claim 12, wherein scaling includes contracting/dilating the calculated morphology based on the underlying heart rate of the PVC beat and a reference heart rate.

14. The method of claim 12, wherein numerically clustering the PVC beats includes utilizing a correlation distance metric to compare morphology signals and cluster PVC beats sharing a similar morphology.

15. The method of claim 12, wherein generating an output includes providing an indication of whether the PVC beats are unifocal or multifocal based on numerical clustering of the PVC beats.

* * * * *